(12) United States Patent
Colvin et al.

(10) Patent No.: US 7,479,126 B1
(45) Date of Patent: Jan. 20, 2009

(54) CANNULA WITH INCISION BLADE

(75) Inventors: Stephen B. Colvin, New York, NY (US);
 Allan Katz, Freeport, NY (US); Eugene A. Grossi, New York, NY (US); Aubrey C. Galloway, Jr., Bronxville, NY (US)

(73) Assignee: Endoscopic Technologies, Inc., San Ramon, CA (US)

( * ) Notice: Subject to any disclaimer, the term of this patent is extended or adjusted under 35 U.S.C. 154(b) by 0 days.

(21) Appl. No.: 11/112,842

(22) Filed: Apr. 22, 2005

Related U.S. Application Data

(60) Provisional application No. 60/623,289, filed on Oct. 29, 2004.

(51) Int. Cl.
 *A61M 31/00* (2006.01)
(52) U.S. Cl. .................................. 604/93.01
(58) Field of Classification Search .............. 604/93.01, 604/264, 272, 274, 96.01, 22, 275; 606/159, 606/170, 167, 180, 184, 26; 128/6
 See application file for complete search history.

(56) References Cited

U.S. PATENT DOCUMENTS

| | | | | |
|---|---|---|---|---|
| 4,869,717 A * | 9/1989 | Adair | ................. | 604/506 |
| 5,234,450 A * | 8/1993 | Segalowitz | ............ | 606/159 |
| 5,354,288 A * | 10/1994 | Cosgrove et al. | ........ | 604/264 |
| 5,406,940 A * | 4/1995 | Melzer et al. | .......... | 600/106 |
| 5,643,226 A * | 7/1997 | Cosgrove et al. | ........ | 604/264 |
| 6,387,087 B1 * | 5/2002 | Grooters | ............... | 604/264 |
| 6,488,693 B2 * | 12/2002 | Gannoe et al. | ......... | 606/167 |
| 6,811,545 B2 * | 11/2004 | Vaillancourt | ........... | 604/158 |
| 2005/0113860 A1 * | 5/2005 | Keidar | ................. | 606/198 |

\* cited by examiner

*Primary Examiner*—Nicholas D Lucchesi
*Assistant Examiner*—Christopher D Koharski
(74) *Attorney, Agent, or Firm*—Sterne, Kessler, Goldstein & Fox P.L.L.C.

(57) ABSTRACT

An apparatus to puncture a blood vessel has an elongate body portion having a first end, a second end, and a lumen. A pusher member is received by the lumen and a gentle flow tip is coupled to the second end. A blade is in communication with the pusher member, wherein the blade is positioned around the outer curvature of the gentle flow tip.

13 Claims, 3 Drawing Sheets

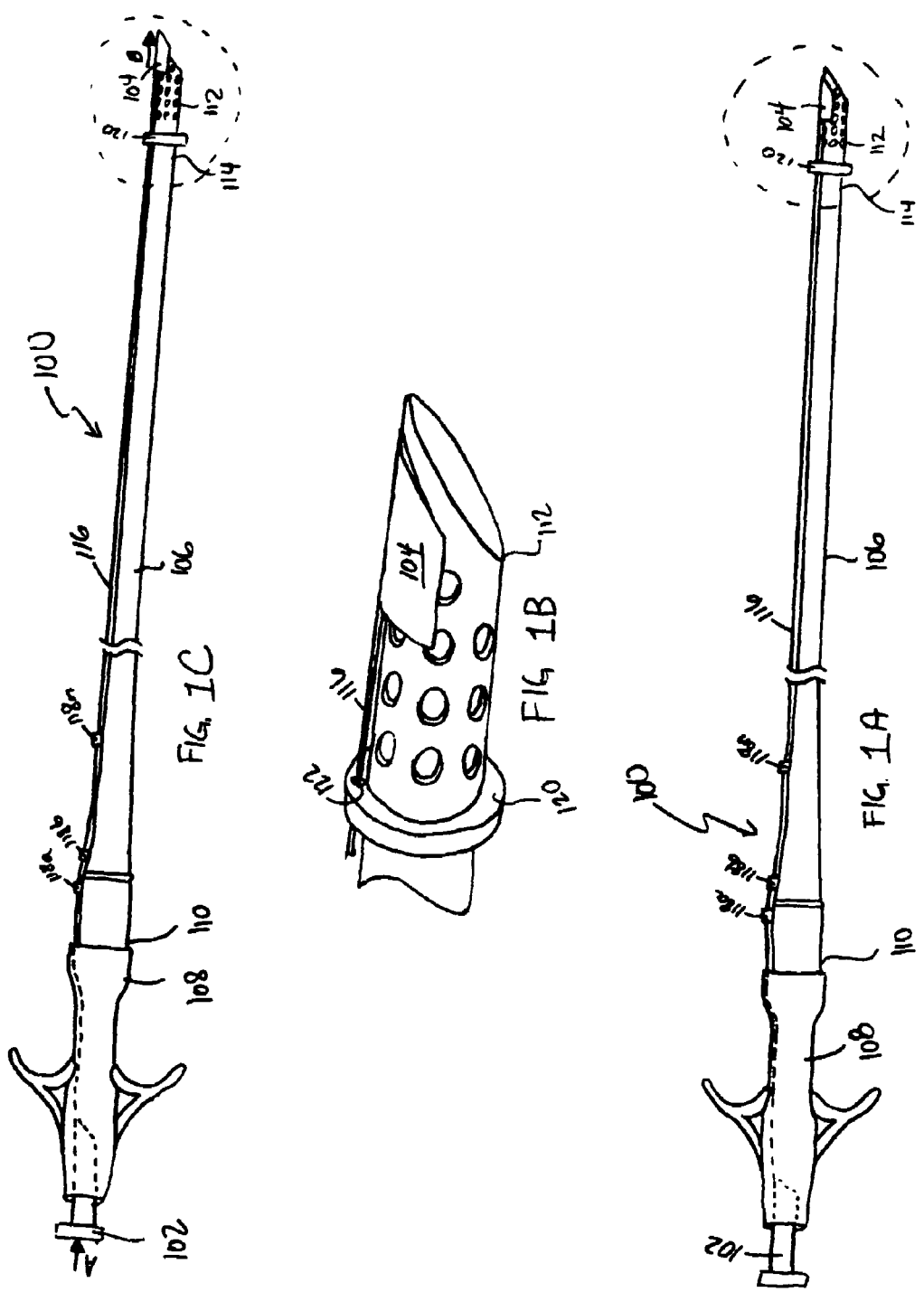

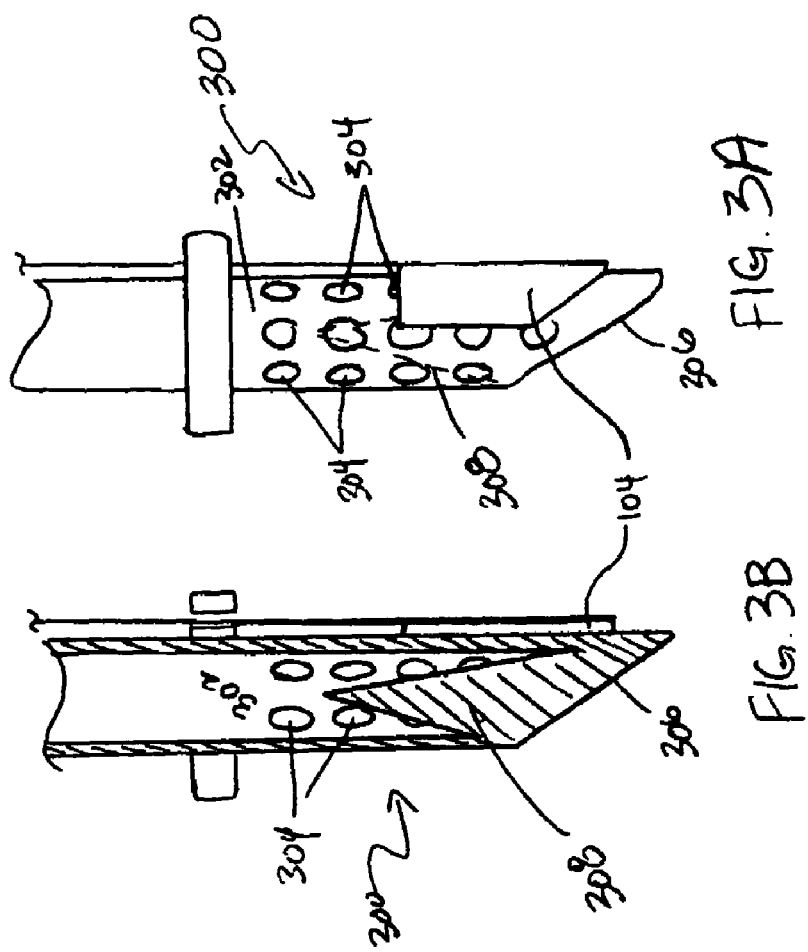
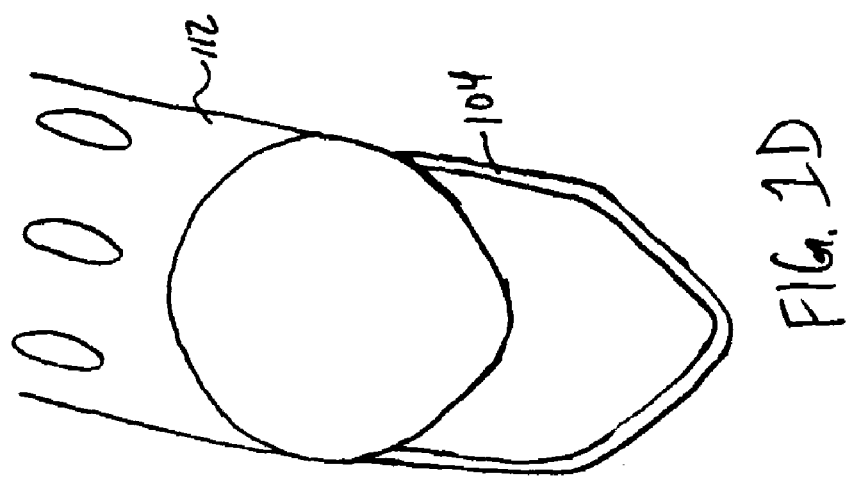

CANNULA WITH INCISION BLADE

CROSS-REFERENCE TO RELATED APPLICATION

This application claims priority based on U.S. Patent Provisional Application Ser. No. 60/623,289, entitled "Cannula With Incision Blade" by Stephen B. Colvin, Alan Katz, Dr. Eugene Grossi and Aubrey C. Galloway, filed on Oct. 29, 2004.

FIELD OF THE INVENTION

The present invention relates to medial devices. More specifically, the present invention relates to cannulas with an incision blade.

BACKGROUND OF THE INVENTION

Cannulae are devices which connect items of hardware or drainage vessels to a patient's body. During heart surgery, for example, a patient's blood is oxygenated and circulated by an artificial heart lung machine. A surgical incision is made into the patient's aorta wherein a cannula is surgically secured such that the outlet end is directed into and along the route of the aorta.

With conventional cannulaes, there have been flow problems associated with the relatively high velocity of blood into the aorta. There are also concerns over the possible dislodgement of fatty tissue from the vicinity of the aorta and its potentially serious implications. Specifically, there is concern that blood emerging at high velocity from cannulae could damage the aortic wall and/or dislodge atheromatous plaque and hence cause embolic phenomena. Additionally, another concern is that high velocities (and related high impact pressures) might disturb the distribution of flow to the blood vessels.

Atheromatous plaque can be released into the general blood circulation when there is cannulation of the aorta, manipulation of the heart and ascending aorta, and application or release of the cross-clamp or side biting clamp to the aorta. Furthermore, boluses of air or "surgical air" can enter the general blood circulation when there is cannulation of the heart or aorta and removal of the cross clamp, at the site of venous cannulation and when a surgical intervention requires the opening of the cardiac chambers. As such, the use of alternative cannulas such as the "soft flow" cannula or "dispersion" cannula have been popular. These cannulas are designed to not have a central flow through a central orifice to avoid having a high velocity jet of blood hitting the back side of the blood vessel wall. However, the velocity of the blood flow from current "soft flow" cannulas are still high, at about 4-6 liters per minute. The gentle flow cannula of the present invention is able to descrease the blood flow even further.

In any type of surgery, especially cardiac surgery, time is of the essence. The less time it takes a surgeon to perform the surgery the better. Currently, incisions are first made into a blood vessel with a surgical knife. The surgical knife is then removed and the cannula is inserted into the incision. The time to perform these two procedures may be drastically reduced by the present invention.

BRIEF DESCRIPTION OF THE INVENTION

An apparatus to puncture a blood vessel has an elongate body portion having a first end, a second end, and a lumen. A pusher member is received by the lumen and a gentle flow tip is coupled to the second end. A blade is in communication with the pusher member, wherein the blade is positioned around the outer curvature of the gentle flow tip.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings:

FIGS. 1A-1D illustrate a gentle flow arterial dispersion cannula with an incision blade in accordance with an embodiment of the present invention.

FIGS. 3A and 3B illustrate the gentle flow tip in accordance with an embodiment of the present invention.

DETAILED DESCRIPTION

Figure 2A:
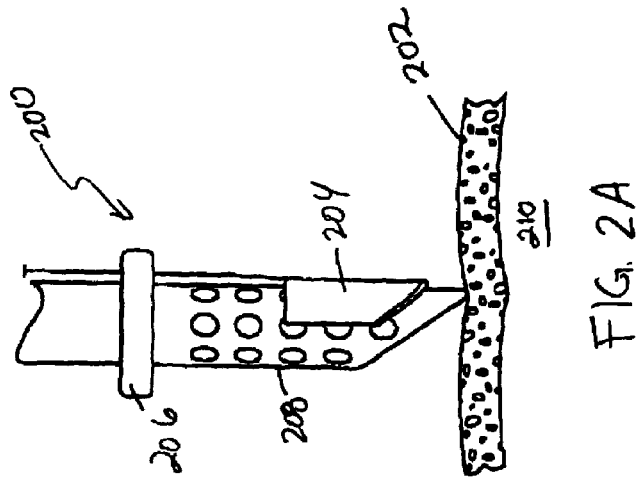
FIGS. 2A, 2B, 2C illustrate the gentle flow arterial dispersion cannula with an incision blade in use with a blood vessel in accordance with an embodiment of the present invention.

Embodiments of the present invention are described herein in the context of a cannula with an incision blade. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure The present invention relates to medical devices such as a cannula with an incision blade for piercing a blood vessel. The present invention may be used for various procedures such as ophthalmology surgery, orthopedic surgery, cardiac surgery, and other procedures that require the puncture of a blood vessel. Thus, the examples described in the present application with reference to cardiac surgery is exemplary and not meant to be limiting. Additionally, the surgical knife may be used with any type of cannula. The example described in the present application with reference to the use of a gentle flow arterial dispersion cannula is exemplary and not intended to be limiting. As such, the incision blade may be used with a traditional cannula, dispersion cannula, and the like.

FIGS. 1A-1D illustrate a gentle flow arterial dispersion cannula with an incision blade in accordance with an embodiment of the present invention. Referring to FIGS. 1A and 1B, the device, generally numbered 100, has a blade pusher 102 in communication with the blade 104 via a blade extension 116.

The blade pusher 102 is inserted into the handle 108 of elongated hollow body portion 106 at a first end 110. A gentle flow tip 112 may be positioned at the second end 114 of the body portion 106.

The blade 104 is positioned such that it is integral with the outer curvature of the device 100 and not on the inside of the device 100. Positioning the blade 104 on the outer curvature of the device 100 rather than through the center or lumen of the device 100 prevents a central flow of blood through the device to avoid the high velocity jet of blood hitting the blood vessel wall. The blade 104 may surround the entire outer curvature of the gentle flow tip 112, however, it is generally not desirable since it will block the blood flow from exiting the gentle flow tip 112. As illustrated in FIG. 1B, the blade 104 surrounds about one-half or less of the entire outer curvature of the gentle flow tip 112.

The blade 104 is connected to the blade pusher 102 through blade extension 116 which is held in position along the outer curvature of the device 100 with holder members 118a, 118b, 118n (where n is an integer). Blade extension 116 is connected to blade pusher 102 within the hollow tube of handle 108. At first end 110, the blade extension 116 exits the hollow tube and is positioned on the exterior outer curvature of device 100.

The holder members 118a, 118b, 118n each have an aperture (not shown) to securely, but loosely, hold the blade extension 116 in place along the outer curvature of the device 100. Holder members 118a, 118b, 118n, although illustrated as projections on the exterior of the device 100, may also surround the circumference of the device 100 similar to stopper member 120. Stopper member 120 may have an aperture 122 to securely, but loosely position the blade extension 116. Additionally, stopper member 120 has a diameter greater than the diameter of the gentle flow tip 112.

As illustrated in FIGS. 1C and 1D, when the blade pusher 102 is pushed in the direction of arrow A, the blade extension 116 is also pushed in the same direction, which causes blade 104 to be pushed in the direction of arrow B. The holder members 118a, 118b, 118n and stopper member 120 loosely, but securely, hold the blade extension 116 in position such that it is movable within the members when the blade pusher 102 is pushed. As further illustrated in FIG. 1D, a front view of the gentle flow tip 112 and blade 104, the blade 104 is positioned along the outer curvature of the gentle flow tip 112.

Figure 2B:
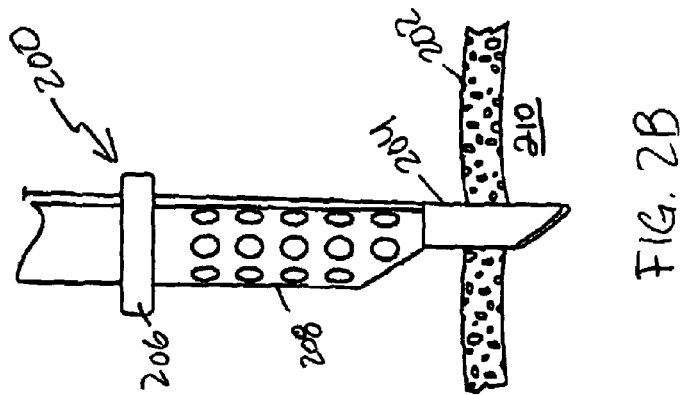
Figure 2C:
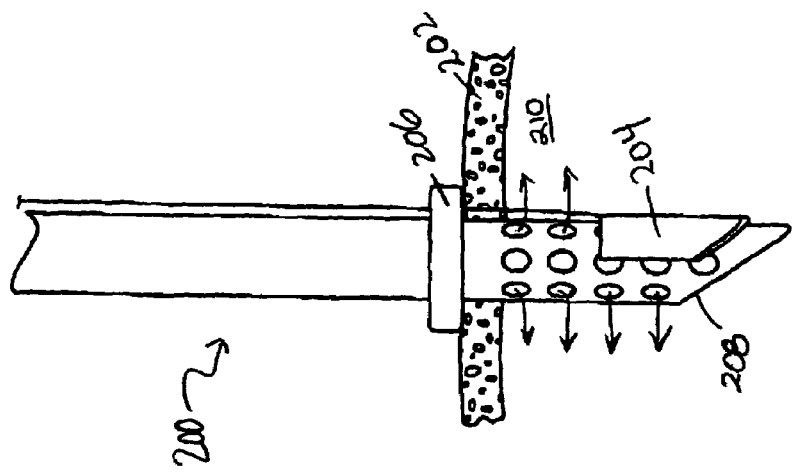

FIGS. 2A, 2B, and 2C illustrate the gentle flow arterial dispersion cannula with an incision blade in use with a blood vessel in accordance with an embodiment of the present invention. As illustrated in FIG. 2A, the device 200 may be placed at the position on the blood vessel 202 where the incision is to be made. Once the desired position is achieved, the user pushes on the blade pusher 102, which causes the blade 204 to puncture the blood vessel 202 at FIG. 2B. Once the blade 204 has punctured the blood vessel 202, the user may insert the gentle flow tip 208 into the blood vessel 202 until stopper member 206 prevents the device 200 from further entering the blood vessel lumen 210 at FIG. 2C. Simultaneously, the user releases the blade pusher 102, which causes the blade 204 to retract to its original position. The gentle flow tip 208 is entirely positioned within the blood vessel lumen 210. The user is able to perform this procedure in one single step rather than in the multiple steps currently required.

FIGS. 3A and 3B illustrate the gentle flow tip in accordance with an embodiment of the present invention. FIG. 3B is a cross sectional view of FIG. 3A. The gentle flow tip, generally numbered 300, has a lumen 302 and a plurality of apertures 304 on the outer curvature of the gentle flow tip 300. The gentle flow tip 300 has an enclosed bottom end 306 and an inverted solid cone 308 within the lumen 302 at the bottom end 306. The inverted solid cone 308 causes the blood to flow outwardly perpendicular to the gentle flow tip 300 and thus parallel the blood vessel lumen 210 (as illustrated in FIG. 2C). This prevents the blood flow exiting the gentle flow tip 300 from damaging the blood vessel wall and/or dislodging any atheromateous plaque which may cause embolic phenomena.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. An apparatus to puncture a blood vessel, comprising:
an elongate body;
a pusher member positioned adjacent to a first end of the elongate body;
a gentle flow tip directly coupled to a second end of the elongate body such that a portion of the elongate body extends between the pusher member and the gentle flow tip, said gentle flow tip having an outer curvature;
a blade positioned around the outer curvature of the gentle flow tip;
a blade extension coupled between the pusher member and the blade, wherein a portion of the blade extension extends along an outer surface of the elongate body; and
a plurality of support members having an aperture to receive at least a portion of the blade extension, wherein the plurality of support members position at least a portion of the blade extension on an exterior of the elongate body.

2. The apparatus of claim 1 further comprising a stopper member positioned at a top end of the gentle flow tip.

3. The apparatus of claim 2 wherein said stopper member further comprises an aperture to receive at least a portion of the blade extension.

4. An apparatus to puncture a blood vessel, comprising:
an elongate body portion having a first end, a second end, and a lumen;
a pusher member received by said lumen;
a gentle flow tip coupled to the second end, said gentle flow tip having an outer curvature;
a blade in communication with the pusher member, wherein the blade is positioned around the outer curvature of the gentle flow tip;
a blade extension coupled between the pusher member and the blade; and
a plurality of support members having an aperture to receive the blade extension, wherein the plurality of support members position the blade extension on an exterior of the elongate body portion.

5. An apparatus to puncture a blood vessel, comprising:
an elongate body having a body lumen, a first end and a second end;
a handle directly coupled to the first end of the elongate body and having a handle lumen in communication with the body lumen;
a pusher member received by said handle lumen;
a gentle flow tip directly coupled to the second end of the elongate body such that the gentle flow tip extends from the second end of the elongate body, said gentle flow tip having an outer curvature;

a blade coupled to the pusher member, wherein the blade is positioned around the outer curvature of the gentle flow tip; and a plurality of support members having an aperture to receive the blade, wherein the plurality of support members position the blade on an exterior of the elongate body.

6. The apparatus of claim 5 further comprising a blade extension coupled between the pusher member and the blade.

7. The apparatus of claim 5 further comprising a stopper member positioned at a top end of the gentle flow tip.

8. The apparatus of claim 7 wherein said stopper member further comprises an aperture to receive the blade extension.

9. The apparatus of claim 5 wherein the gentle flow tip further comprises a plurality of apertures positioned along the outer curvature.

10. The apparatus of claim 5 wherein the gentle flow tip further comprises a lumen having an inverted cone positioned within the lumen at the bottom end.

11. An apparatus to puncture a blood vessel, comprising:
an elongate body;
a handle coupled to the elongate body;
a pusher member coupled adjacent to the handle;
a gentle flow tip coupled to the elongate body and having an outer curvature;
a blade positioned around the outer curvature of the gentle flow tip;
a blade extension coupled between the pusher member and the blade;
a plurality of support members having an aperture to receive the blade extension, wherein the plurality of support members position the blade extension on an exterior of the elongate body.

12. An apparatus to puncture a blood vessel, comprising:
an elongated member having a first end, a second end, and an outer surface;
a pusher member disposed adjacent to the first end of the elongated member;
a blade disposed on the outer surface of the elongated member near the second end of the elongated member, wherein the blade is coupled to the pusher member so as to allow the pusher member to actuate the blade and thereby move the blade relative to the elongated member; and
a plurality of support members having an aperture to receive the blade, wherein the plurality of support members position the blade on an exterior of the elongate body.

13. The apparatus of claim 12, wherein the elongated member further comprises a lumen and
a tip disposed adjacent to the second end of the elongated member, wherein the tip includes a cone-shaped projection extending into the lumen of the elongated member.

* * * * *